(12) United States Patent
Lee et al.

(10) Patent No.: US 7,153,998 B2
(45) Date of Patent: Dec. 26, 2006

(54) METHOD FOR REFINING 2,6-NAPHTHALENE DICARBOXYLIC ACID

(75) Inventors: Jong-In Lee, Seongnam (KR);
Hyun-Sup Shim, Seoul (KR);
Yong-Jun Shin, Seoul (KR);
Hang-Duk Roh, Ansan (KR)

(73) Assignee: SK Chemical Co., Ltd. (KR)

( * ) Notice: Subject to any disclaimer, the term of this patent is extended or adjusted under 35 U.S.C. 154(b) by 0 days.

(21) Appl. No.: 10/523,265

(22) PCT Filed: May 9, 2003

(86) PCT No.: PCT/KR03/00917

§ 371 (c)(1),
(2), (4) Date: Feb. 1, 2005

(87) PCT Pub. No.: WO2004/013071

PCT Pub. Date: Feb. 12, 2004

(65) Prior Publication Data

US 2005/0261518 A1    Nov. 24, 2005

(30) Foreign Application Priority Data

Aug. 1, 2002   (KR) ...................... 10-2002-0045525

(51) Int. Cl.
*C07C 51/42* (2006.01)

(52) U.S. Cl. ..................................... 562/486

(58) Field of Classification Search ..................... None
See application file for complete search history.

(56) References Cited

U.S. PATENT DOCUMENTS

| 5,344,969 A | 9/1994 | Iwane et al. ................. 562/486 |
| 5,859,294 A * | 1/1999 | Hashimoto et al. ......... 562/486 |
| 6,291,707 B1 | 9/2001 | Lin ............................. 562/485 |

FOREIGN PATENT DOCUMENTS

| EP | 1055660 A1 | 11/2000 |
| JP | 07-118200 | 5/1995 |
| WO | WO 98/12157 | 3/1998 |

* cited by examiner

*Primary Examiner*—Paul A. Zucker
(74) *Attorney, Agent, or Firm*—Gifford, Krass, Groh, Sprinkle, Anderson & Citkowski, P.C.

(57) ABSTRACT

The present invention relates to a method for refining 2,6-naphthalene dicarboxylic acid, and particularly to a method for refining 2,6-naphthalene dicarboxylic acid comprising recrystallizing crude 2,6-naphthalene dicarboxylic acid in the form of an amine salt using a solvent comprising a protic polar solvent selected from the group consisting of an alcohol, water, and a mixture thereof, and an acetate. In accordance with the invention, 2,6-naphthalene dicarboxylic acid can be obtained with excellent purity and color, and at the same time, it can be obtained in an economical and environmentally friendly way because the acetate, which is a byproduct of the oxidation process, is used as a solvent.

13 Claims, No Drawings

METHOD FOR REFINING 2,6-NAPHTHALENE DICARBOXYLIC ACID

BACKGROUND OF THE INVENTION (a) Field of the Invention

The present invention relates to a method for refining 2,6-naphthalene dicarboxylic acid, and more particularly, to a method for refining 2,6-naphthalene dicarboxylic acid capable of obtaining a product having excellent purity and color in an economical and environmentally friendly manner.

(b) Description of the Related Art

Polyesters produced by the polymerization of 2,6-naphthalene dicarboxylic acid with a diol are known to excel in several properties such as thermal stability, tensile strength, gas permeability, etc., and as such are chosen as good materials for films, fibers, storage containers, etc. In particular, polyethylene naphthalate (PEN) produced by the polymerization of 2,6-naphthalene dicarboxylic acid and ethylene glycol is expected to replace polyethylene terephthalate (PET).

2,6-Naphthalene dicarboxylic acid is obtained by oxidizing 2,6-dimethyl naphthalene with oxygen gas in the presence of catalytic cobalt, manganese, and bromine compounds. The thus-obtained crude 2,6-naphthalene dicarboxylic acid contains numerous impurities including acids having one functional group such as formyl naphthoic acid, methyl naphthoic acid, etc. that are generated by incomplete oxidation of 2,6-dimethyl naphthalene; trimellitic acid that is obtained from the collapse of naphthalene structure; and brominated naphthalene dicarboxylic acid, naphthoic acid, naphthalene tricarboxylic acid, colored organic impurities whose structures are not identified, and metal impurities such as cobalt complex, manganese complex, etc.

Polyesters obtained by the polymerization of ethylene glycol and crude 2,6-naphthalene dicarboxylic acid containing impurities as mentioned above show poor physical properties, heat stability, structural stability, and so on. Moreover, such polyesters are classified as low quality because they are tinged with color.

Of the impurities, mono carboxylic acids such as methyl naphthoic acid, naphthoic acid, etc. are especially problematic. If these mono carboxylic acids exceed a certain amount, the polymerization rate is decreased during the production of polyesters, and gelation and coloring occur. In particular, formyl naphthoic acid is especially problematic. Accordingly, so as to obtain polyesters having high quality, it is important to reduce these impurities.

2,6-Naphthalene dicarboxylic acid cannot be refined by distillation because it is degraded at high temperature, and it is not easy to refine it by re-crystallization because it is not dissolved well in general solvents.

Until now, several refinement methods of 2,6-naphthalene dicarboxylic acid have been known. The first method is to dissolve 2,6-naphthalene dicarboxylic acid in general solvents and then recrystallize it. The second method is to convert 2,6-naphthalene dicarboxylic acid into its alkali salt and then dissolve and recrystallize it. The third method is to convert 2,6-naphthalene dicarboxylic acid into its amine salt and then dissolve and recrystallize it. Also, industrially, pure dimethyl 2,6-naphthalene dicarboxylate is produced by reacting 2,6-naphthalene dicarboxylic acid with methanol to prepare dimethyl 2,6-naphthalene dicarboxylate (2,6-NDC) and then refining it through distillation to be sold. However, as can be seen in the preparation of polyethylene terephthalate resins, as raw materials for the synthesis of polyesters, acids are superior to esters in processing and economics, and therefore studies on methods capable of directly refining 2,6-naphthalene dicarboxylic acid in a convenient and economical manner are required.

As a known method for refining 2,6-naphthalene dicarboxylic acid by dissolving it in general solvents and then recrystallizing it, U.S. Pat. No. 5,256,817 discloses a method for refining 2,6-naphthalene dicarboxylic acid by dissolving it in water or acetic acid and then hydrogenating and crystallizing it. However, as this method requires heating to a high temperature in order to dissolve the 2,6-naphthalene dicarboxylic acid, the production cost of naphthoic acid is increased and it also requires expensive metal catalysts for hydrogenation, and is thus problematic.

Japanese Patent Publication No. 62-230747 A discloses a method of dissolving 2,6-naphthalene dicarboxylic acid in polar solvents such as dimethylsulfoxide, dimethylformamide, dimethylacetamide, etc., adsorbing it to activated carbons, hydrogenating it, and then crystallizing it. However, such method requires a quantity of solvents and activated carbons, the solvents may be hydrogenated, and the formyl naphthoic acid is not eliminated and thus the yield of the products is low. Japanese Patent Publication No. 5-32586 A discloses a method for refining 2,6-naphthalene dicarboxylic acid by dissolving it using pyridine or pyridine derivatives as a solvent and then crystallizing it, but this method is also problematic because the solubility of 2,6-naphthalene dicarboxylic acid in the solvents is not sensitive to temperature and its yield is thus low.

As another method for refining 2,6-naphthalene dicarboxylic acid, there is a method of converting it into its metal salt and then dissolving and recrystallizing it. Japanese Patent Publication No. 52-20993 A and Japanese Patent Publication No. 48-68544 B disclose a method for refining 2,6-naphthalene dicarboxylic acid by dissolving it in a KOH or NaOH aqueous solution to thereby prepare its alkali metal salt, then adsorbing it with a solid adsorbent and crystallizing it. Disproportionation of the thus-produced mono alkali salt with water generates a refined 2,6-naphthalene dicarboxylic acid. However, this method requires a quantity of solid adsorbents and solvents, and as all mono alkali salts are crystallized, salts generated by impurities such as naphthoic acid or formyl naphthoic acid, etc. are also crystallized and it is difficult to separate them.

Japanese Patent Publication No. 52-20994 B and Japanese Patent Publication No. 48-68555 B disclose a method for refining 2,6-naphthalene dicarboxylic acid using a diacid salt. This method is carried out by dissolving 2,6-naphthalene dicarboxylic acid in a KOH or NaOH aqueous solution, then adsorbing it to an adsorbent and crystallizing the produced diacid salt. However, this method also requires a large amount of adsorbents, it is difficult to eliminate a small amount of alkali salt impurities, and it has a low yield. Japanese Patent Publication No. 2-243652 A discloses a method of dissolving 2,6-naphthalene dicarboxylic acid in an alkali aqueous solution and then precipitating an alkali salt by adding a polar organic solvent that is well mixed with water thereto, but when 2,6-naphthalene dicarboxylic acid having high purity is obtained, it has the problem that its yield is low.

There are proposed methods of dissolving 2,6-naphthalene dicarboxylic acid into the form of its amine salt and then recrystallizing it. The produced 2,6-naphthalene dicarboxylic acid in the form of an amine salt is heated to a temperature above the boiling point of the amine to thereby generate pure 2,6-naphthalene dicarboxylic acid. Japanese Patent Publication No. 50-142542 A discloses a method of dissolving 2,6-naphthalene dicarboxylic acid in an amine aqueous solution and then precipitating 2,6-naphthalene dicarboxylic acid in the form of an amine salt by distilling and concentrating the solvent. Japanese Patent Publication No. 50-135062 A discloses a method of dissolving 2,6-naphthalene dicarboxylic acid in an amine aqueous solution and then precipitating it by cooling or condensing the solution, and Japanese Patent Publication No. 5-294892 A discloses a method of obtaining pure 2,6-naphthalene dicarboxylic acid by dissolving 2,6-naphthalene dicarboxylic acid in a mixed solution of an alcohol and an amine, then precipitating it with an amine salt and heating it. However, these methods have the problem that when 2,6-naphthalene dicarboxylic acid having a high purity is obtained, its yield is low.

U.S. Pat. No. 5,859,294 discloses a method of obtaining pure 2,6-naphthalene dicarboxylic acid by mixing 2,6-naphthalene dicarboxylic acid with an amine, dissolving it in a mixed solution of water, a ketone, or acetonitrile, cooling it to thereby precipitate the diamine salt of 2,6-naphthalene dicarboxylic acid, and then distilling it. However, this method has the problem of requiring a high temperature and high pressure to obtain 2,6-naphthalene dicarboxylic acid with a high yield.

Therefore, study on methods for refining 2,6-naphthalene dicarboxylic acid capable of obtaining 2,6-naphthalene dicarboxylic acid having excellent purity and color in a convenient and economical manner are urgently required.

SUMMARY OF THE INVENTION

This invention provides a method for refining 2,6-naphthalene dicarboxylic acid capable of obtaining 2,6-naphthalene dicarboxylic acid having excellent purity and color.

The present invention provides a method for refining 2,6-naphthalenedicarboxylic acid comprising recrystallizing crude 2,6-naphthalenedicarboxylic acid in the form of an amine salt using a solvent comprising a protic polar solvent selected from the group consisting of an alcohol, water, and a mixture thereof, and an acetate.

DETAILED DESCRIPTION OF THE PREFERRED EMBODIMENTS

This invention will hereafter be described in detail.

The inventors found that during the study on a refinement method capable of obtaining 2,6-naphthalene dicarboxylic acid having high purity, as a result of the recrystallization of crude 2,6-naphthalene dicarboxylic acid in the form of an amine salt using a protic polar solvent selected from the group consisting of an alcohol, water, and a mixture thereof together with an acetate, 2,6-naphthalene dicarboxylic acid having a high purity could be obtained with a high yield, and hence, based on such findings, they completed the subject invention.

The refinement method of the invention is characterized in that crude 2,6-naphthalene dicarboxylic acid in the form of an amine salt is refined by recrystallizing it using a mixed solution of a protic polar solvent selected from the group consisting of an alcohol, water, and a mixture thereof, and an acetate.

The crude 2,6-naphthalene dicarboxylic acid obtained from the oxidation reaction of 2,6-dimethyl naphthalene contains impurities including metal complexes of cobalt and manganese, bromine compounds generated by the bromination of naphthalene structure, etc, monoacids such as formyl naphthoic acid, naphthoic acid, etc., and other colored organic compounds. The bromine compounds corrode the reactor, monoacids inhibit the polymerization reaction, and the colored organic compounds deteriorate the color of the products and thus have an adverse effect on their quality. The present invention enables 2,6-naphthalene dicarboxylic acid having excellent purity and color to be obtained in an environmentally friendly and economical manner by refining it using a protic polar solvent selected from the group consisting of an alcohol, water, and a mixture thereof together with an acetate after converting the crude 2,6-naphthalene dicarboxylic acid containing such compounds into its amine salt.

According to the first preferred embodiment of the invention, the refinement of 2,6-naphthalene dicarboxylic acid is carried out by the following procedures of (a) adding an amine to crude 2,6-naphthalenedicarboxylic acid to form a mixture; (b) dissolving the mixture of (a) in a protic polar solvent selected from the group consisting of an alcohol, water, and a mixture thereof to obtain an amine salt solution of 2,6-naphthalene dicarboxylic acid; (c) filtering the amine salt solution of (b) at a high temperature to form a filtrate, adding an acetate to the filtrate, and cooling the filtrate to obtain an amine salt crystal of 2,6-naphthalene dicarboxylic acid; and (d) filtering and heating the amine salt crystal of 2,6-naphthalene dicarboxylic acid of (c) to deaminate the salt.

According to the second preferred embodiment of the invention, the refinement of 2,6-naphthalenedicarboxylic acid is carried out by the following procedures of (a) adding an amine to crude 2,6-naphthalene dicarboxylic acid to form a mixture; (b) adding a mixed solvent comprising a protic polar solvent selected from the group consisting of an alcohol, water, and a mixture thereof, and an acetate to the mixture of (a) and then dissolving the mixture-by heating to obtain an amine salt solution of 2,6-naphthalene dicarboxylic acid; (c) cooling the amine salt solution of (b) to room temperature to obtain an amine salt crystal of 2, 6-naphthalene dicarboxylic acid; and (d) filtering, heating, and drying the amine salt crystal of 2,6-naphthalene dicarboxylic acid of (c) to deaminate the salt.

According to the third preferred embodiment of the invention, the refinement of 2,6-naphthalene dicarboxylic acid is carried out by the following procedures of (a) adding an amine to crude 2,6-naphthalene dicarboxylic acid to form a mixture; (b) adding a mixed solvent including a protic polar solvent selected from the group consisting of an alcohol, water, and a mixture thereof, and an acetate to the mixture of (a) and then dissolving the mixture by heating to obtain an amine salt solution of 2,6-naphthalenedicarboxylic acid; (c) filtering the amine salt solution of (b) at a high temperature to form a filtrate and then cooling the filtrate to room temperature to obtain an amine salt crystal of 2,6-naphthalene dicarboxylic acid; and (d) filtering, heating, and drying the amine salt crystal of 2,6-naphthalenedicarboxylic acid of (c) to deaminate the salt.

In the preferred first to third embodiments of the invention, the process of adding an amine to crude 2,6-naphthalene dicarboxylic acid is preferably carried out under the conditions of room temperature and room pressure.

The amine used in the invention is to be used to form a diamine salt with no special restrictions on its type, but in consideration of cost, specific heat, and so on, it is preferable to use ammonia, trimethyl amine, triethyl amine, diethyl amine, dimethyl amine, methyl amine, or ethyl amine.

The amine is required in an amount of more than one equivalent, preferably 10 to 1.2 equivalents with regard to each functional group of 2,6-naphthalenedicarboxylic acid. The amine that reacts with 2,6-naphthalenedicarboxylic acid and forms a salt can be recovered by cooling when the salt is deaminated by heating.

The solvent used in the invention is a protic polar solvent selected from the group consisting of an alcohol, water, and a mixture thereof, and an acetate. Of the protic polar solvent, the alcohol and water are preferably used in a ratio of 1:1 to 100:1 by weight, and the solvent is the protic polar solvent and acetate preferably in a 1:1 to 1:20 ratio of protic polar solvent to acetate by weight.

The protic polar solvent selected from the group consisting of an alcohol, water, and a mixture thereof well dissolves the amine salt of 2,6-naphthalene dicarboxylic acid, whereas it is difficult for the acetate to dissolve the amine salt of 2,6-naphthalene dicarboxylic acid. However, the mixed solution containing these two kinds of solvents has high solubility at a high temperature, as the solubility constant of the amine salt of 2,6-naphthalene dicarboxylic acid therein is high at a high temperature but it has low solubility at a low temperature, and accordingly it is desirable for recrystallization. Also, in the case that such solvent is used, 2,6-naphthalene dicarboxylic acid can be refined with a high yield of not less than 90%. The longer the length of alkyl chains at both ends of the ester becomes, the more solvents are needed. This is because the solubility of the amine salt of 2,6-naphthalene dicarboxylic acid becomes reduced as the length of alkyl chains becomes longer.

There are no special restrictions on the type of the acetate, but particular examples include methyl acetate (MA), ethyl acetate (EA), normal propyl acetate (n-PA), and isopropyl acetate (i-PA).

Of the exemplified acetates, methyl acetate is generated as a byproduct in oxidation reaction when acetic acid is used as a solvent, like the process for preparing terephthalic acids by oxidizing paraxylene. Likewise, it is generated during the preparation of the starting material of the invention, crude 2,6-naphthalene dicarboxylic acid, and accordingly, in the case that it is used as a solvent, it has economical and environmentally friendly advantages because the costs required for treating acetate and purchasing other solvents are saved. In addition, the invention also has energy-saving effects in that acetate with a specific heat that is not relatively high is used, and methyl alcohol with a specific heat that is lower than that of water is used as a solvent to dissolve 2,6-naphthalene dicarboxylic acid.

Of the refinement method of the invention, when 2,6-naphthalene dicarboxylic acid in the form of amine salt is dissolved in the above solvent, the dissolution is preferably carried out at a temperature within the range of 25~150° C., and the cooling for crystallizing the amine salt of 2,6-naphthalene dicarboxylic acid is preferably carried out at a temperature within the range of −10~50° C.

In accordance with the refinement method of the invention as described above, 2,6-naphthalene dicarboxylic acid having excellent purity and color can be obtained. Also, the invention enables the refinement of 2,6-naphthalene dicarboxylic acid in an easy and convenient manner as well as in an environmentally friendly and energy-saving way, by re-using solvents that are used during the refinement process and by using a byproduct of the reaction process as a solvent. In addition, the invention has industrially applicable advantages by decreasing the amounts of naphthoic acid, formyl naphthoic acid, and the remaining catalyst compounds in impure 2,6-naphthalene dicarboxylic acid.

To facilitate the understanding of the invention, preferred examples thereof are provided. However, these examples are provided solely to illustrate the invention; the scope of the invention should not be construed to be limited thereto.

EXAMPLES

Example 1

To a 1-neck Erlenmeyer flask having a Pyrex-type lid, 30.0 g of crude 2,6-naphthalene dicarboxylic acid and 33.4 g of triethyl amine were added at room temperature and room pressure. At 50° C., 60 g of methanol were added to the above mixture, which was then stirred for 30 minutes to obtain a solution of the amine salt of 2,6-naphthalene dicarboxylic acid. After the amine salt solution was filtrated using a filter with a 7-μm pore size, 240 g of methyl acetate was added to the filtrate to mix them, and the resultant was then cooled at 0° C. for 12 hours. The amine salt crystal of 2,6-naphthalene dicarboxylic acid obtained after cooling was filtrated and deaminated at 90° C. to yield a purified 2,6-naphthalene dicarboxylic acid.

The contents of bromine compounds, cobalt, and manganese remaining in the obtained 2,6-naphthalene dicarboxylic acid were determined, and the yield, purity, and color of 2,6-naphthalene dicarboxylic acid were determined, and the results are shown in Table 1 below. The purity was determined using G.C.

TABLE 1

| Category | | Ex. 1 |
|---|---|---|
| Solvent | MeOH (g) | 60 |
|  | MA (g) | 240 |
| Cooling Temperature (° C.) | | 0 |
| Yield (%) | | 66.2 |
| Purity (%) | | 99.31 |
| Color (Color-b) | | 2.15 |
| T-Br (ppm) | | 87 |
| Co (ppm) | | 24 |
| Mn (ppm) | | 2 |

Example 2

After 30.0 g of crude 2,6-naphthalene dicarboxylic acid and 33.4 g of triethyl amine were added to a 4-neck Erlenmeyer flask having a Pyrex-type lid at room temperature and room pressure, 315 g of a mixed solution containing methanol and methyl acetate in a mixing ratio of 2:8 were added thereto and the mixture was heated to 55° C. while stirring for 30 minutes to obtain a solution of the amine salt of 2,6-naphthalene dicarboxylic acid. The amine salt solution was placed at room temperature for 12 hours to thereby crystallize it, and the thus-produced diamine salt crystal of 2,6-naphthalene dicarboxylic acid was then filtrated and deaminated at 90° C. to yield a refined 2,6-naphthalene dicarboxylic acid powder.

The contents of bromine compounds, cobalt, and manganese remaining in the obtained 2,6-naphthalene dicarboxylic acid, and the yield, purity, and color of 2,6-naphthalene dicarboxylic acid were determined in the same manner as in Example 1 above, and they are shown in Table 2 below.

TABLE 2

| Category | Ex.2 |
|---|---|
| Solvent (wt. %) | MeOH:MA = 20:80 |
| Solvent Amount (g) | 315 |
| Yield (%) | 27.6 |
| Purity (%) | 99.75 |
| Color (Color-b) | 1.14 |
| T-Br (ppm) | 288 |

TABLE 2-continued

| Category | Ex.2 |
|---|---|
| Co (ppm) | 693 |
| Mn (ppm) | 44 |

Examples 3~4

The procedures were carried out in the same manner as used in Example 2 above, except that the mixed solution wherein methanol:water:acetate were mixed in a mixing ratio of 2:0:8 to be used as a solvent in Example 2 was replaced by those having the contents shown in Table 3 below. In addition, the type of acetate varied by each example.

The contents of bromine compounds, cobalt, and manganese remaining in the 2,6-naphthalene dicarboxylic acid obtained in Examples 3 to 4 above, and the yield, purity, and color of 2,6-naphthalene dicarboxylic acid were determined in the same manner as in Example 1 above, and they are shown in Table 3 below.

TABLE 3

| Category | Ex. 3 | Ex. 4 |
|---|---|---|
| Solvent (wt. %) | MeOH:$H_2$O:MA = 1.5:0.5:8.0 | MeOH:$H_2$O:EA = 1.5:0.5:8.0 |
| Solvent Amount (g) | 405 | 390 |
| Yield (%) | 74.7 | 82.5 |
| Purity (%) | 99.46 | 99.54 |
| Color (Color-b) | 3.11 | 2.87 |
| T-Br (ppm) | 99.6 | 98.7 |
| Co (ppm) | 521 | 417 |
| Mn (ppm) | 31 | 25 |

Examples 5~8

The procedures were carried out in the same manner as used in Example 2 above, except that the mixed solution wherein methanol:water:acetate were mixed in a mixing ratio of 2:0:8 to be used as a solvent in Example 2 was replaced by those having the contents shown in Table 4 below. In addition, the type of acetate varied by each example.

The contents of bromine compounds, cobalt, and manganese remaining in the 2,6-naphthalene dicarboxylic acid obtained in Examples 5 to 8 above, and the yield, purity, and color of 2,6-naphthalene dicarboxylic acid were determined in the same manner as in Example 1 above, and they are shown in Table 4 below.

TABLE 4

| Category | Ex. 5 | Ex. 6 | Ex. 7 | Ex. 8 |
|---|---|---|---|---|
| Solvent (wt. %) | MeOH:$H_2$O:MA = 1.75:0.25:8.00 | MeOH:H2O:EA = 1.75:0.25:8.00 | MeOH:$H_2$O:n-PA = 1.75:0.25:8.00 | MeOH:H2O:i-PA = 1.75:0.25:8.00 |
| Solvent Amount (g) | 270 | 325 | 370 | 500 |
| Yield (%) | 68.1 | 78.5 | 78.0 | 77.7 |
| Purity (%) | 99.58 | 99.62 | 99.46 | 99.67 |
| Color (Color-b) | 2.01 | 1.85 | 1.99 | 2.53 |
| T-Br (ppm) | 100 | 86 | 77 | 73 |
| Co (ppm) | 647 | 739 | 1024 | 914 |
| Mn (ppm) | 46 | 46 | 59 | 51 |

Example 9

After 50.0 g of crude 2,6-naphthalene dicarboxylic acid and 56.5 g of triethyl amine were added to a 4-neck Erlenmeyer flask having a Pyrex-type lid at room temperature and room pressure, 315 g of a mixed solution containing methanol:water:methyl acetate in a mixing ratio of 1.75: 0.25:8.00 were added thereto and the mixture was then heated to 55° C. while stirring for 1 hour to obtain a solution of the amine salt of 2,6-naphthalene dicarboxylic acid. The amine salt solution was filtered using a filter with a 7 μm pore size at 60° C. under a reduced pressure, the thus-obtained filtrate was heated to 55° C. for 30 minutes to convert it into its solution form, and then it was placed for 12 hours to thereby crystallize it. The thus-produced diamine salt crystal of 2,6-naphthalene dicarboxylic acid was filtrated and deaminated at 90° C. to yield a refined 2,6-naphthalene dicarboxylic acid powder.

Examples 10~11

The procedures were carried out in the same manner as used in Example 9 above, except that ethyl acetate and n-PA were respectively used, instead of methyl acetate.

The contents of bromine compounds, cobalt, and manganese remaining in the 2,6-naphthalene dicarboxylic acid obtained in Examples 9 to 11 above, and the yield, purity, and color of 2,6-naphthalene dicarboxylic acid were determined in the same manner as in Example 1 above, and they are shown in Table 5 below.

TABLE 5

| Category | Ex. 9 | Ex. 10 | Ex. 11 |
|---|---|---|---|
| Solvent (wt. %) | MeOH:$H_2$O:MA = 1.75:0.25:8.00 | MeOH:$H_2$O:EA = 1.75:0.25:8.00 | MeOH:$H_2$O:n-PA = 1.75:0.25:8.00 |
| Solvent Amount (g) | 450 | 500 | 530 |
| Yield (%) | 62.2 | 63.6 | 67.3 |
| Purity (%) | 99.57 | 99.71 | 99.69 |
| Color (Color-b) | 3.60 | 1.89 | 2.36 |
| T-Br (ppm) | 84 | 116 | 109 |
| Co (ppm) | 21 | 182 | 162 |
| Mn (ppm) | 2 | 12 | 8 |

In accordance with the invention, 2,6-naphthalene dicarboxylic acid can be obtained with excellent purity and color. In addition, as the solvent used in the refinement process is re-used and the byproduct of the reaction process is used as a solvent, this invention is environmentally friendly and has energy-saving effects. Further, it enables the refinement of pure 2,6-naphthalene dicarboxylic acid in an easy and economical way by eliminating the naphthoic acid, formyl naphthoic acid, catalyst compounds, etc. remaining in impure 2,6-naphthalene dicarboxylic acid.

What is claimed is:

1. A method for refining 2,6-naphthalene dicarboxylic acid comprising recrystallizing an amine salt of 2,6-naphthalene dicarboxylic acid using a solvent comprising a protic polar solvent selected from the group consisting of an alcohol, water, and a mixture thereof, and an acetate; and
    deaminating the amine salt of 2,6-naphthalene dicarboxylic acid to yield the refined 2,6-naphthalene dicarboxylic acid.

2. A method for refining 2,6-naphthalene dicarboxylic acid further comprising
    (a) adding an amine to crude 2,6-naphthalene dicarboxylic acid to form a mixture;
    (b) dissolving the mixture of (a) in a protic polar solvent selected from the group consisting of an alcohol, water, and a mixture thereof to obtain an amine salt solution of 2,6-naphthalene dicarboxylic acid;
    (c) filtering the amine salt solution of (b) to form a filtrate, adding an acetate to the filtrate, and cooling the filtrate to obtain an amine salt crystal of 2,6-naphthalene dicarboxylic acid; and
    (d) filtering and heating the amine salt crystal of 2,6-naphthalene dicarboxylic acid of (c) to deaminate the salt.

3. A method for refining 2,6-naphthalene dicarboxylic acid comprising
    (a) adding an amine to crude 2,6-naphthalene dicarboxylic acid to form a mixture;
    (b) adding a mixed solvent comprising a protic polar solvent selected from the group consisting of an alcohol, water, and a mixture thereof, and an acetate to the mixture of (a) and then dissolving the mixture by heating to obtain an amine salt solution of 2,6-naphthalene dicarboxylic acid;
    (c) cooling the amine salt solution of (b) to room temperature to obtain an amine salt crystal of 2,6-naphthalene dicarboxylic acid; and
    (d) filtering, heating, and drying the amine salt crystal of 2,6-naphthalene dicarboxylic acid of (c) to deaminate the salt.

4. A method for refining 2,6-naphthalene dicarboxylic acid further comprising
    (a) adding an amine to crude 2,6-naphthalene dicarboxylic acid to form a mixture;
    (b) adding a mixed solvent comprising a protic polar solvent selected from the group consisting of an alcohol, water, and a mixture thereof, and an acetate to the mixture of (a) and then dissolving the mixture by heating to obtain an amine salt solution of 2,6-naphthalenedicarboxylic acid;
    (c) filtering the amine salt solution of (b) at a high temperature to form a filtrate and then cooling the filtrate to room temperature to obtain an amine salt crystal of 2,6-naphthalenedicarboxylic acid; and
    (d) filtering, heating, and drying the amine salt crystal of 2,6-naphthalenedicarboxylic acid of (c) to deaminate the salt.

5. The method for refining 2,6-naphthalene dicarboxylic acid of claim 2, wherein in said protic polar solvent, an alcohol and water are used in a ratio of 1:1 to 100:1 by weight.

6. The method for refining 2,6-naphthalene dicarboxylic acid of claim 2 wherein said protic polar solvent and acetate are used in a ratio of 1:1 to 1:20 by weight.

7. The method for refining 2,6-naphthalene dicarboxylic acid of claim 2, wherein said dissolution of the mixture is carried out at a temperature within the range of 25–150° C., and the cooling is carried out at a temperature within the range of −10–50° C.

8. The method for refining 2,6-naphthalene dicarboxylic acid of claim 3, wherein said dissolution of the mixture is carried out at a temperature within the range of 25–150° C., and the cooling is carried out at a temperature within the range of −10–50° C.

9. The method for refining 2,6-naphthalene dicarboxylic acid of claim 4, wherein said dissolution of the mixture is carried out at a temperature within the range of 25–150° C., and the cooling is carried out at a temperature within the range of −10–50° C.

10. The method for refining 2,6-naphthalene dicarboxylic acid of claim 3, wherein in said protic polar solvent, an alcohol and water are used in a ratio of 1:1 to 100:1 by weight.

11. The method for refining 2,6-naphthalene dicarboxylic acid of claim 3, wherein said protic polar solvent and acetate are used in a ratio of 1:1 to 1:20 by weight.

12. The method for refining 2,6-naphthalene dicarboxylic acid of claim 4, wherein in said protic polar solvent, an alcohol and water are used in a ratio of 1:1 to 100:1 by weight.

13. The method for refining 2,6-naphthalene dicarboxylic acid of claim 4, wherein said protic polar solvent and acetate are used in a ratio of 1:1 to 1:20 by weight.

* * * * *

UNITED STATES PATENT AND TRADEMARK OFFICE
CERTIFICATE OF CORRECTION

| | |
|---|---|
| PATENT NO. | : 7,153,998 B2 |
| APPLICATION NO. | : 10/523265 |
| DATED | : December 26, 2006 |
| INVENTOR(S) | : Jong-in Lee et al. |

It is certified that error appears in the above-identified patent and that said Letters Patent is hereby corrected as shown below:

Column 9, line 32, before "comprising" insert --acid--

Signed and Sealed this

Tenth Day of April, 2007

JON W. DUDAS
*Director of the United States Patent and Trademark Office*